United States Patent
Bradford et al.

(10) Patent No.: US 6,342,656 B1
(45) Date of Patent: Jan. 29, 2002

(54) REGULATION OF SOURCE-SINK RELATIONSHIPS AND RESPONSES TO STRESS CONDITIONS IN PLANTS

(75) Inventors: Kent J. Bradford; Peetambar Dahal; Hong Yang, all of Davis; Michael Cooley, Benicia, all of CA (US); Bruce Downie, Lexington, KY (US); Oliver Henry Gee, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/359,161

(22) Filed: Jul. 21, 1999

(51) Int. Cl.[7] .................. A01H 5/00; C12N 15/29; C12N 15/82; C12N 15/84; C12P 19/00
(52) U.S. Cl. ................ 800/284; 800/278; 800/289; 800/298; 800/317.4; 536/23.6; 435/320.1; 435/419; 435/411; 435/468; 435/194
(58) Field of Search ................... 800/284, 286, 800/289, 298, 317.4; 536/23.6, 24.5; 435/410, 411, 419, FOR 16 D, 194, 468, 320.1

(56) References Cited

PUBLICATIONS

Abe, H. et al., Accession #U40713, Journal, Nov. 14, 1995.*
Lan, V. et al., "The Electronic Plant Gene Register." Plant Physiol, p. 335–337, 1996.*
Yang, H. et al., "Expression of a SNF4–like protein kinase–related gene in tomato seeds." Poster Sessions, Plant Physiology, vol. 114, No. 3, p. 270.*
Purcell P. et al., "Antisense expression of a sucrose non–fermenting–1–related protein kinase sequence in potato results . . . and loss of sucrose–inducibility of sucrose synthase transcripts in leaves." Plant J. 14, pp. 195–202, 1998.*
Arndt, G. et al., "Colocalization of antisense RNAs and ribozymes with their target mRNAs." Genome, vol. 40, pp. 785–797, 1997.*
Stam, M. et al., "The Silence of Genes in Transgenic Plants.", Annals of Botany, 79, pp. 3–12, 1997.*
Old, R., Primrose, S., "Principles of Gene Manipulation–An Introduction to Genetic Engineering.", Studies in Microbiology, pp. 18–20 and 65–69, 1994.*
Bork, P. "Powers and Pitfalls in Sequence Analysis: The 70% Hurdle. " 2000, Genome Research, pp. 398–400.*
Burgess, W. H. et al., "Possible Dissociation of the Heparin–binding and Mitogenic Activities of Heparin–binding (Acidic Fibroblast) . . . of a Single Lysine Residue." 1990, The J. of Cell Biology, vol. 111, pp. 2129–2138.*
Bowie, J. U. et al., "Deciphering the Message in Protein Sequences: Tolerance to Amino Acid Substitutions." 1990, Science, vol. 247, pp. 1306–1310.*
Broun, P. et al., "Catalytic Plasticity of Fatty Acid Modification Enzymes Underlying Chemical Diversity of Plant Lipids." 1998, Science, vol. 282, pp. 1315–1317.*

* cited by examiner

*Primary Examiner*—David T. Fox
*Assistant Examiner*—Anne R Kubelik
(74) *Attorney, Agent, or Firm*—Townsend and Townsend and Crew, LLP

(57) ABSTRACT

The invention provides the identification and characterization of plant SNF4 and SNF1 genes. Examples of the genes were cloned from tomato. They are nucleic acids and proteins belonging to the SNF1-related protein kinase family, and are involved in plant's response to stress conditions such as nutritional and environmental stresses. The invention also provides transgenic plants containing the genes, and methods of modulating stress responses in transgenic plants comprising these genes.

17 Claims, 3 Drawing Sheets

```
LeSNF4    MQATAEIQAAGSPRRSQKHQMLKDKQVKDLIIDKRRLVEVPYTATLADTINTIMANKVAVPPGHWIGAGGSMILE
          80
Pv42      MQE......VKGATMQRSRSVRLKEKKVKDMMVGKKRLVEVPYTASLAQIMNTLVANKIVAVPPGQWIGAGGSMIVE
          75
AMPK-γ    MES....VAAESAPAPENEHSQE.................TESNSSVYTEMKSHRCYDLIETSSKLVVEDTSLQVK
          57
SNF4      MKP....TQDSQEKVSIEQ..................QLAVESIRKELNSKTSYDVLPVSYRLIVLDTSLLVK
          51

LeSNF4    SDKQTGAVRKHYIGMVTMLDILAYEAGNGMRDDDDIT....KKMMVPVSSIIGHCLESLSIMTLSP.NTSIVDCMEVFS
          155
Pv42      SDKQTGAVRKHYIGMVTMLDILAHIAGDDHISCGDNITQDLDQRMSDSVSSIIGHSFEGISIMTINE.NTSMIDCMEVFS
          154
AMPK-γ    KA................FFALVINGVRAAPLWDS....KKQSFVGMLITTDFINITHRYYKSA.LVQYELEEHKI
          113                                                                      1/3
SNF4      KS................INVILQNSIVSAPLWDS....KTSRFAGLLTTTDFINVIQYYFSNDKFELVDKIQLDG
          108

LeSNF4    KGIHRAMVPVNGRLENVV.GVEITESASCYRMLTQMDLIRFLN.DQQEIKAIMSHKVSDKQLQAITDTVFGVTNKARVID
          233
Pv42      KGVHRAMVPVDGLFENVASGVEITESASSYQMLTQMDMLKEIHGGGAEIHSILSRSVQD..LGADTVQYAIIDRTKIVH
          232
AMPK-γ    ETWRENVYLQDSFKPLVCISPNASIFDAVSSLIRNKIHRLPVIDPESGNTLYILTHKRI...LKFLKLITEFPKPEFMSK
          190
SNF4      LKDIERALGVDQLDTASIHPSRPLFEACLKMLESRSGRIPLIDQEETHREIVVSVLTQ..YRIIKFVALNCRETHFLKI
          186
```

FIG. 1.

```
LeSNF4  VIKCMRTASLNAVPIVESSNDITEDHTQLVNGKKRKI.VGTFSATDLRGCPVSKMQPLINLEVLDFLK.......MLSGAE
        306
Pv42    AIKCLKAMLNAVPIVRATGVGQDDHKQLINGRCRKI.IGTFSATDLRGCHISLKSWLGISAAAETEEVRSSPLYSESD
        311
AMPK-γ  SIEELQIGTYANIAMVRITTPVYVALGIFMQHRVSALPVVDEKGRVVDIYSKFDVINIAAEKTYNND.......VSVTKA
        264
SNF4    PIGDENITTQDNMKSCQMTTPVLDVIQMTTQGRVSSVPIIDENGYLINVYEAYDVLGLIKGGIYNDLS.......LSVGEA
        260

LeSNF4  NTGLRSSWREQVTCRPESSLGEVVEKVMSDNVHRVWVVDEQGLIEGVVSLTDMIRVIRLWYLTEFL.Q
        373
Pv42    MQNRGSSRRELVTCYAESPLSEVIERAVTSHVHRVWVVDQEGLLVGVVSLTDVIRVIRHSLSDSNDQ
        379
AMPK-γ  LQHRSHYFEGVLKCYLHETIEAIINRLMEAEVHRLVVVDEHDVVKGIVSLSDIIQAIVLTG.GEKK.P
        330
SNF4    IMRRSDDEGVYTCTKNDKLSTIMDNIRKARVHRFFVVDDVGRLVGVLTLSDILKYIIIGS.N
        322
```

*FIG. 1.* (CONTINUED)

REGULATION OF SOURCE-SINK RELATIONSHIPS AND RESPONSES TO STRESS CONDITIONS IN PLANTS

STATEMENT AS TO RIGHTS TO INVENTIONS MADE UNDER FEDERALLY SPONSORED RESEARCH AND DEVELOPMENT

This invention was made with Government support under Grant Nos. IBN-9407264 and UBN-9722978 awarded by the National Science Foundation. The Government has certain rights in this invention.

BACKGROUND OF THE INVENTION

Cells must sense their nutritional or environmental conditions and modify their metabolic activity appropriately. Yeast SNF1 (sucrose non-feirmenting) protein kinase and mammalian AMP-activated protein kinase (AMPK) are central components of kinase cascades that act as metabolic sensors of glucose availability and AMP:ATP levels respectively. Protein sequence and functional homology exists between the yeast and mammalian kinase subunits (SNF1/AMPK-α), activation subunits (SNF4/AMPK-γ) and the docking subunits (SIP/AMPK-β) that constitute the functional kinase complexes (Hardie, D., et al., *Annu. Rev. Biochem.* 67:821–55 (1998)).

In yeast, the association of the SNF4 activating subunit with a regulatory region of the SNF1 protein is sensitive to glucose. When glucose concentration is low, the SNF4 protein associates with the regulatory domain of SNF1, and the activity of the catalytic kinase domain is increased, resulting in the derepression of genes required for the metabolism of alternative energy sources. When glucose concentration is high, the SNF1 kinase domain associates with its regulatory domain and kinase activity is inhibited. In mammals, the activation of AMPK, in response to increases in the AMP:ATP ratio, results in the switching on of ATP-producing pathways and the switching off of ATP-consuming pathways. For example, AMPK activation results in the phosphorylation and inactivation of acetyl coenzyme A carboxylase and 3-hydroxy-3-30 methylglutaryl coenzyme A reductase (HMGCoA reductase); but unlike in yeast, the specific functions of the γ- and β-subunits are less well defined.

In plants, there is also evidence that carbohydrates control gene expression, growth, metabolism and differentiation. Jang and Shcen, *Trend's in Plant Sciences*, 2:208–214 (1997); Koch, *Annu. Rev. Plant. Physiol. Mol.*, 2:509–540 (1996)). An extensive family of SNF1 homologs and related kinases have been characterized and have been grouped into several subfamilies of SNF1-related kinases (SnRKs) (Halford, et al., *Plant Mol. Biol.* 37:735–748 (1996)). In addition to exhibiting kinase activity on substrates common to the mammalian and yeast kinases and complementing yeast SNF1 mutants (Alderson, et al. *Proc. Natl. Acad. Sci. U.S.A.* 88:8602–05 (1991); Muranaka, et al. *Mol. Cell Biol.*, 14:2958–65 (1994)), antisense suppression experiments suggest that plant SNF1 homologs may also be involved in regulation of carbon metabolism in planta. Purcell, et cal., *Plant J.* 14:195 (1998). However, NPK5,a SNF1 homolog from tobacco was unable to complement an SNF4-deletion yeast mutant strain (Δ-SNF4), suggesting that NPK5 may require an SNF4-like component for physiological activity in vivo (Muranaka et al., *Mol Cell Biol.*, 14:2958–65 (1994)).

No functional homolog of the SNF4 activating subunit has yet been demonstrated from plants, although a gene sequence (Pv42) isolated from developing bean seeds was reported to have predicted amino acid sequence similarity to SNF4. (Accession No. U40713.) Thus, there exist needs to identify and express plant homologs to yeast SNF4 proteins in order to understand how plants cope with metabolic and strcss conditions in the environment and to modulate these responses to engineer plants resistant to various environmental stresses. In addition, production of genetically engineered plants with improved carbon metabolism and source-sink relationships could be used to improve yields or qualities of harvested plant products. The present invention addresses these and other needs.

SUMMARY OF THE INVENTION

The present invention provides SNF4 homologs from plants. In particular, the present invention provides nucleic acid molecules which encode plant SNF4 polypeptides. The polypeptides of the invention comprise an amino acid sequence that has greater than about 70% identity to SEQ ID NO:3.

Also provided is the promoter sequence from SEQ ID NO:2. Promoters of the invention can be operably linked to heterologous nucleic acid sequences and used to drive expression of the heterologous sequences in desired plant tissues.

The present invention further provides SNF1 polypeptides. The SNF1 polypeptides of the invention comprise an amino acid sequence that has greater than about 95% identity to the amino acid sequence of the polypeptide encoded by SEQ ID NO:4. An exemplary SNF1 nucleic acid molecule from tomato is shown in SEQ ID NO:4 (LeSNF1). Preferably, the nucleic acid molecule can specifically hybridize to SEQ ID NO:4 or its complement.

The present invention fuirther provides recombinant expression vectors comprising the nucleic acid sequences of the invention. Preferably, the vectors comprise a plant promoter operably linked to the nucleic acid sequence. The promoter can be either a constitutive promoter, or an inducible promoter.

The present invention also provides for transgenic plants comprising a recombinant expression cassette of the invention. The recombinant expression cassettes are useful in methods of modulating source-sink relationships in plants and thereby enhancing yield or quality of harvested plant products, such as fruit. For example, the nucleic acids of the invention can be used to enhance sink activity and starch or lipid accumulation in seeds. Alternatively, the can be used to enhance sugar accumulation in fruit. The expression cassettes of the invention can also be used to enhance responsiveness to stress conditions in plants.

DEFINITIONS

The term "stress conditions" as used herein generally refers to nutritional and environmental stress that plants encounter in their life cycle. Examples of stress conditions are any nutritional or environmental changes that lead to changes in plant internal metabolic pathways and alterations in the plant's carbon reserves. Examples of environmental stresses include extreme temperature (e.g. excess heat or cold), high salt, flooding, anoxia, drought, toxic chemicals (e.g. herbicides, heavy metals) and the like.

The term "plant SNF4 polypeptide" refers to plant homologs of yeast SNF4. Without wishing to be bound by theory it is believed that the polypeptides of the invention are activating subunits in kinase cascades that act as metabolic sensors of carbohydrate availability and ATP levels in plant cells The proteins of the invention are a component in SNF1 related protein kinases which are composed of kinase subunits (SNF1), activation subunits (SNF4), and docking subunits (SIP). The term "LeSNF4" refers to plant SNF4 polypeptides derived from tomato (*Lycopersicon escuentum*).

Plant SNF4 polypeptides of the invention are typically from about 20 amino acids to about 400 amino acids in length, usually from about 100 to about 375, and often from about 200 to about 300 amino acids. A full length plant SNF4 polypeptide of the invention is typically about 375 amino acids.

The term "plant SNF1 polypeptide" refers to a plant homolog of the SNF1 subunit of the SNF1-related protein kinase. An example of a SNF1 nucleic acid is the LeSNF1 nucleic acid sequence as shown in SEQ ID NO.:4. An example of a SNF1 amino acid sequence is the LeSNF1 amino acid sequence as shown in SEQ ID NO.:5.

The phrase "nucleic acid sequence" refers to a single or double-stranded polymer of deoxyribonucleotide or ribonucleotide bases read from the 5' to the 3 end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells. Such a promoter can be derived from plant genes or from other organisms, such as viruses capable of infecting plant cells.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endospenn, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include Agrobatcterium-mediated transformation, biolistic methods, electroporation, and the like. Such a plant containing the exogenous nucleic acid is referred to here as a $T_1$ (e.g. in Adrabidopsis by vacuum infiltration) or $R_0$ (for plants regenerated from transformed cells in vitro) generation transgenic plant. Transgenic plants that arise from sexual cross or by selfing are descendants of such a plant.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Clonincg-A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 70%, more preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When usinlg a sequence comparison algonrthm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acidcs Res.* 25: 3389–3402, respectively. Software for performing BLAST analyses is publicly available through the National Center for Biotechiology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Nalt. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations, " which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);

3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biolooy—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Lower stringency conditions are generally selected to be about 15–30 ° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for shoit probes (e.g., 10 to 50 nucleotides) and at least about 60° C. for long probes (e.g., greater than 50 nucleotides). Stringent conditions may also be achieved with the addition of destabilizing agents such as fonnamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, gcnomic DNA or cDNA comprising plant SNF4 or SNF1 nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1X SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

BRIEF DESCRIPTION OF THE DRAWINGS

FIG. 1 shows the predicted amino acid sequences of LeSNF4 (SEQ ID NO:3), Pv42 (SEQ ID NO:5), AMPK-γ (SEQ ID NO:6) and SNF4 (SEQ ID NO:7). Identical amino acids and conservative substitutions are boxed. CBS domains are underlined. Alignment was by the J. Hein method using a structural weight table (Megalign software, DNAStar, Inc., Madison Wis.).

FIG. 2A—In yeast, SNF1 and SNF4 interact to form a complex with one of a family of proteins (SIP1/SIP2/GAL83). Each of these latter proteins can independently interact with SNF4 at an association domain (ASC) and with SNF1 at a kinase interacting sequence (KIS). When glucose is high, interaction between the KD and RD of SNF1 autoinhibits its kinase activity. When glucose is low, SNF4 interacts with the RD of SNF1, activating the KD region. There is also evidence that SNF1 is phosphorylated (indicated by the P group) under derepressing conditions (low glucose) by a SNF1 activating factor homologous to a kinase known to activate AMPIK in mammals. FIG. 2B—The yeast SNF1 protein is composed of a kinase domain (KD) and a regulatory domain (RD). The regulatory domain can interact with the kinase domain of the same protein and the SNF4 protein. The NPK5 protein is a plant homolog of SNF1 from tobacco. StubbGAK83 is a plant homolog from potato of the yeast SIP/GAL proteins (Lakatos et al. 'Plant J. 17:569–574 (1999)). Experimental evidence indicates that all the interaction shown with solid arrows occur in vivo, indicating conservation of these functions in plants and yeast. The α subunit of the mammalian AMP activated protein kinase (AMPK) is a homolog of SNF1, the γ-subunit is a homolog of SNF4 and the β subunit is a homolog of SIP/GAL. This figure is updated from Jiang and Carlson Genes Dev 10:3105–3115 (1996).

DESCRIPTION OF THE SPECIFIC EMBODIMENTS

Introduction

Figure 2A:
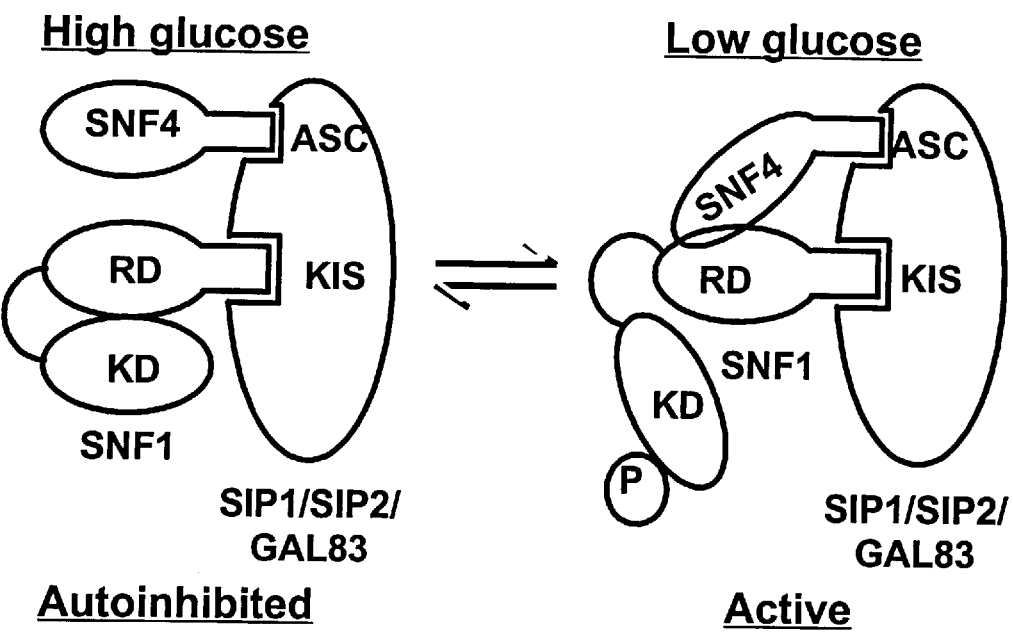
FIGS. 2A and 2B are schematic representations of the yeast SNF1/SNF4 complex in yeast and homologs in plants and mammals.
Figure 2B:
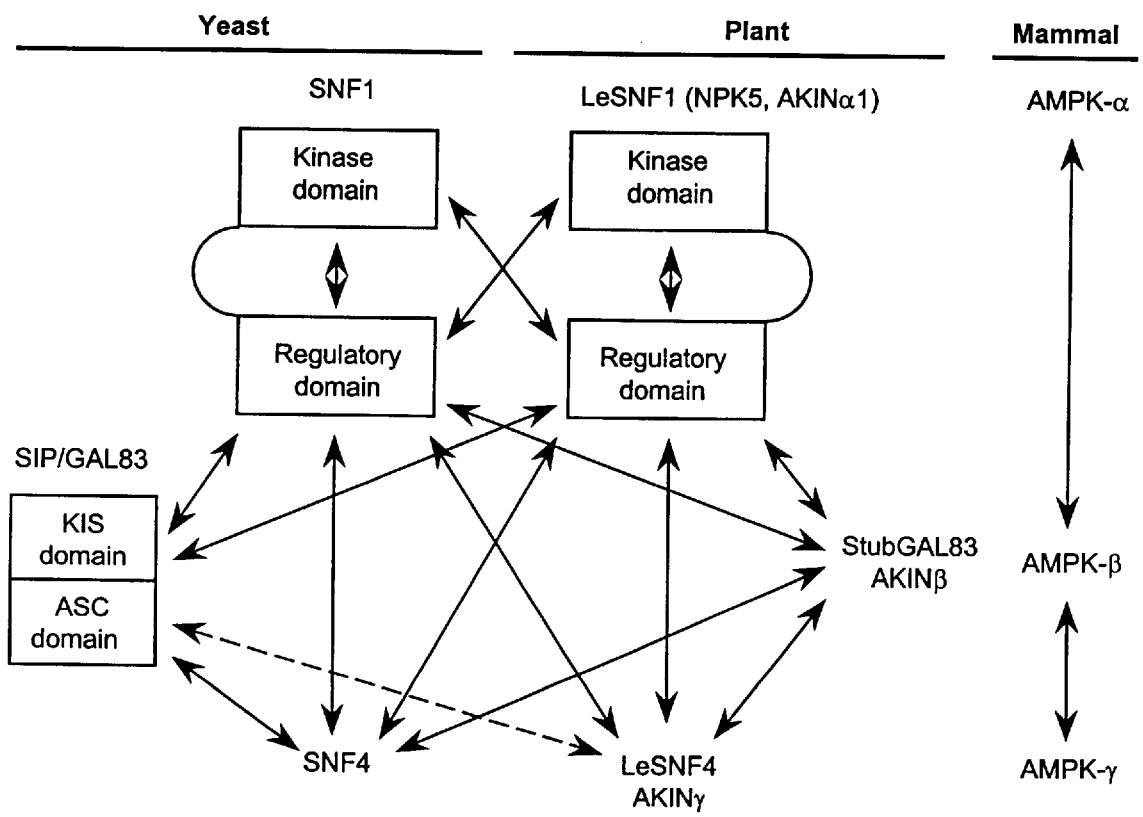

The AMP-activated/SNF1 protein kinase family is conserved across mammals, plants and yeast and plays a critical role in cellular metabolic responses to nutritional or environmental stress. Members of this family are protein kinase components of kinase cascades that act as metabolic sensors of glucose availability and AMP: ATP levels (see, FIG. 2). Structurally, SNF-1 related protein kinases are composed of kinase subunits (SNF1), activation subunits (SNF4), and docking subunits (SIP/GAL83), all three constituting the functional protein kinase complex. SNF4 activating subunits (such as those claimed here) associate with a regulatory region of the SNF1 protein, and regulate the activity of the protein kinase is response to sugar level. Since SNF1 protein kinases play a critical role in response to nutritional and environmental stress, the polynucleotides of the invention can be used to modulate source-sink relationships and responses to stress conditions in plants.

Increasing Polvpeptide Activity or Gene Expression

Any of a number of means well known in the art can be used to increase activity of SNF1 or SNF4 polypeptides or polynucleotides of the invention in plants. Enhanced expression is useful, to alter expression of sugar related genes or to enhance resistance to stress. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endospern, and seed coat) and fruit. Alternatively, one or several genes of the invention can be expressed constitutively (e.g., usinig the CaMV 35S promoter).

Usually isolated sequences prepared as described herein are used to prepare recombinant expression cassettes in recombinant vectors. The vectors are introduced into plant cells using methods well known to those of skill in the art. Preparation of suitable constructs and means for introducing them into plants are described below.

One of skill will recognize that the polypeptides encoded by the nucleic acids of the invention, like other proteins, have different domains that perform different functions. Thus, gene sequences of the invention need not be full length, so long as the desired functional domain of the protein is expressed.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

Alternatively, endogenous SNF4 or SNFP genes can be modified to enhance expression of these genes. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays, fast neutrons or gamma rays can be used.

Alternatively, homologous recombination can be used to induce targeted gene modifications by specifically targeting gene of the invention in vivo (see, generally, Grewal and Klar, *Genetics* 146:1221–1238 (1997) and Xu et al., Geines Dev. 10:2411–2422 (1996)). Homologous recombination has been demonstrated in plants (Puchta et al., Experienitia 50: 277–284 (1994), Swoboda et al., *EMBO J*. 13: 484–489 (1994); Offringa et al., *Proc. Natl. Acaci. Sci. USA* 90: 7346–7350 (1993); and Kempin et al. Natutre 389:802–803 (1997)).

Other means for increasing activity of polynucleotides and polypeptides of the invention can also be used. For example, one method to increase expression of genes of the invention is to use "activation mutagenesis" (see, e.g. Hiyashi et al. Science 258:1350–1353 (1992)). In this method an endogenous gene of the invention can be modified to be expressed constitutively, ectopically, or excessively by insertion of T-DNA sequences that contain strong/constitutive promoters upstream of the endogenous gene.

Inhibition of Activity or Expression of Polynucleotides or Polvpeptides of the Invention Activity of endogenous SNF1 or SNF4 genes can also be inhibited using well known techniques. Inhibition of expression of these genes can be used, for instance, to modulate the activity of enzymes associated with sugar metabolism. For example, inhibition of these genes can be used to inhibit sucrose synthase and inducibility of this enzyme (see, e.g. Purcell et al. Plant Journal 14:195–202 (1998)). In seeds, inhibition of SNF4 expression can be used to break dormancy and stimulate germination. Selective or tissue specific inhibition can be used to alter carbon metabolic pathways, for example.

The nucleic acid sequences disclosed here can be used to design nucleic acids useful in a number of methods to inhibit expression of genes of the invention in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque, *Plant Sci. (Limerick)* 105:125–149 (1995); Pantopoulos, In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al., *Plant Sci. (Shannon)* 127: 61–69 (1997)) and by preventing the accumulation of mRNA which encodes the protein of interest, (see, Baulcombe, *Plant Mol. Bio*. 32:79–88 (1996); Prins and Goldbach,*Arch.* Virol. 141: 2259–2276 (1996); Metzlaff et al. *Cell* 88: 845–854 (1997), Sheehy et al., *Proc. Nat. Acaci. Sci. USA*, 85:8805–8809 (1988), and Hiatt et al., U.S. Pat. No. 4,801, 340).

The nucleic acid segment to be introduced generally will be substantially identical to at least a portion of the endogenous gene or genes (e.g., LeSNF4, or LeSNF1, etc.) to be repressed. The sequence, however, need not be perfectly identical to inhibit expression. The vectors of the present invention can be designed such that the inhibitory effect applies to other genes within a family of genes exhibiting identity or substantial identity to the target gene.

For antisense suppression, the introduced sequence also need not be full length relative to either the primary transcription product or fully processed mRNA. Generally, higher identity can be used to compensate for the use of a shorter sequence. Furthermore, the introduced sequence need not have the same intron or exon pattern, and identity of non-coding segments may be equally effective. Normally, a sequence of between about 30 or 40 nucleotides to about the full length of a nucleotide should be used, though a sequence of at least about 100 nucleotides is preferred, a sequence of at least about 200 nucleotides is more preferred, and a sequence of about 500 to about 3500 nucleotides is especially preferred.

A number of gene regions can be targeted to suppress expression of genes of the invention. The targets can include, for instance, the coding regions, introns, sequences from exon/intron junctions, 5' or 3' untranslated regions, and the like.

Another well-known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al., *Plant Mol. Bio.* 22:1067–1085 (1993); Flavell, *Proc. Natl. Acacd. Sci. USA* 91:3490–3496 (1994); Stam et al., *Annals Bot.* 79:3–12 (1997); Napoli et al., *The Plant Cell* 2:279–289 (1990); and U.S. Pat. Nos. 5,034 323, 5,231,020, and 5, 283, 184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity is most preferred. As with antisense regulation, the effect should apply to any other proteins within a similar family of genes exhibiting identity or substantial identity.

For co-suppression, the introduced sequence, needing less than absolute identity, also need not be full length, relative to either the primary transcription product or fully processed mRNA. This may be preferred to avoid concurrent production of some plants that over-express the introduced sequence. A higher identity in a sequence shorter than full-length compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targeted using co-suppression technologies.

Other means of inhibiting expression are known. These methods include formation of triple-helix DNA (see, e.g., Havre and Glazer *J. Virology* 67:7324–7331 (1993); Scanlon et al. FASEB J. 9:1288–1296 (1995); Giovannangeli et al. *Biochemistry* 35:10539–10548 (1996); Chan and Glazer *J. Mol. Meclicine* (Berlin) 75:267–282 (1997)) and ribozymes (Zhao and Pick, Nature 365:448–451 (1993); Eastham and Ahlering, *J Urology* 156:1186–1188 (1996); Sokol and MulTay, *Transgenic Res.* 5:363–371 (1996); Sun et al., *Mol. Biotechnology* 7:241–251 (1997); and Haseloffet al., *Nature*, 334:585–591 (1988)).

Modification of endogenous SNF1 or SNF4 genes can also be used to inhibit expression. Methods for introducing genetic mutations described above can also be used to select for plants with decreased expression of genes of the invention.

Other means for inhibiting polynucleotide or polypeptide activity can also be used. Activity of polynucleotides of the invention may be modulated by eliminating the proteins that are required for cell-specific expression of such polynuclcotides. Thus, expression of regulatory proteins and/or the sequences that control gene (e.g. LeSNF4 or LeSNF1) expression can be modulated using the methods described here.

Purification of Polypeptides

Naturally occurring or recombinant polypeptides of the invention can be purified for use in functional assays. Naturally occurring polypeptides can be purified, e.g., from plant tissue and any other source of the desired polypeptide. Recombinant polypeptides can be purified from any suitable expression system.

The polypcptides of the invention may be purified to substantial purity by standard techniques, including selective precipitation with such substances as ammonium sulfate; column chromatography, immunopurification methods, and others (see, e.g., Scopes, *Protein Purification. Principles and Practice* (1982); U.S. Pat. No. 4,673,641; Ausubel et al., supra; and Sambrook et al., supra).

A number of procedures can be employed when recombinant polypeptides are being purified. For example, proteins having established molecular adhesion properties (e.g. epitope tags, histidine tags and the like) can be reversibly fused to polypeptides of the invention. With the appropriate ligand, the such polypeptides can be selectively adsorbed to a purification column and then freed from the column in a relatively pure form.

Isolation of Nucleic Acids of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligasc, DNA polymerasc, restriction cndonucleases and the like are performed according to the manufacturer's specifications. These techniques and various other techniques are generally performed according to Sambrook el al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of nucleic acids of the invention may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library that contains a gene transcript of the invention is prepared from the mRNA. Alternatively, cDNA may be prepared from mRNA extracted from other tissues in which genes of the invention or homologs are expressed.

The cDNA or genomic library can then be screened using a probe based upon the sequence of a cloned gene of the invention as disclosed here. Probes may be used to hybridize with genomic DNA or cDNA sequences to isolate homologous genes in the same or different plant species. Alternatively, antibodies raised against a polypeptide of the invention can be used to screen an mRNA expression library.

Alternatively, the nucleic acids of interest can be amplified from nucleic acid samples using amplification techniques. For instance, polymerase chain reaction (PCR) technology can be used to amplify the sequences of genes of the invention directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see *PCR Protocols: A Guide to Methods and Applications*. (Innis, M, Gelfand, D., Sninsky, J. and White, T., eds.), Academic Press, San Diego (1990). Appropriate primers and probes for identifying sequences of the invention from plant tissues are generated from comparisons of the sequences provided here (e.g. SEQ ID NO:1, SEQ ID NO:3, etc.).

Polynucleotides may also be synthesized by well-known techniques as described in the technical literature. See, c.g., Carruthers et al., Cold Spring Harbor Symp. Quant. Biol. 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Preparation of Recombinant Vectors

To use isolated sequences in the above techniques, recombinant DNA vectors suitable for transfonnation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexprcssion, a plant promoter fragment may be employed which will direct expression of the gene in all tissues of a regenerated plant. Such promoters are refelTed to herein as "constitutive" promoters and are active under most environmental conditions and states of development or cell differentiation. Examples of constitutive promoters include the cauliflower mosaic virus (CaMV) 35S transcription initiation region, the 1'-or 2'-promoter derived from T-DNA of *Agrobacterium tumefaciens*, and other transcription initiation regions from various plant genes known to those of skill. Constitutive promoters and regulatory elements can also be isolated from genes that are expressed constitutively or at least expressed in most if not all tissues of a plant. Such genes include, for example, ACT11 from Arabidopsis (Huang et al. *Plant Mol. Biol.* 33:125–139 (1996)), Cat3 from Arabiclopsis (GenBank No. U43147, Zhong et al., *Mol. Gen. Genet.* 251:196–203 (1996)), the gene encoding stearoyl-acyl carrier protein desaturase from Brassica napus (Genbank No. X74782, Solocombe et al. *Plant Physiol.* 104:1167–1176 (1994)), GPcl from maize (GenBank No. X15596, Martinez et al. *J. Mol. Biol.* 208:551–565 (1989)), and Gpc2 from maize (GenBank No. U45855, Manjunath et al., *Plant Mol. Biol.* 33:97–112 (1997)).

Alteniatively, the plant promoter may direct expression of a nucleic acid of the invention in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or application of chemicals/honnones (such promoters can be used, for example, in the chemical induction of antisense SNF4 sequences for breaking seed donnancy). Tissue-specific promoters may only promote transcription within a certain time frame of developmental stage within that tissue. Other tissue specific promoters may be active throughout the life cycle of a particular tissue. One of skill will recognize that a tissue-spccific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissuc-specific promoters can be used in the invention. For instance, promoters that direct expression of nucleic acids in leaves, roots or flowers are useful for enhancing resistance to pathogens that infect those organs. For example, seed-specific promoters (e.g., promoters from seed storage protein genes) can be used to direct expression of the polynucleotides of the invention and thereby enhance sink activity and starch or lipid accumulation in seeds. Alternatively, fruit specific promoters can be used to direct expression in fruit and thereby enhance sugar accumulation in fruit. For expression of a polynucleotide of the invention in the aerial vegetative organs of a plant, photosynthetic organ-specific promoters, such as the RBCS promoter (Khoudi, et al., *Gene* 197:343, 1997), can be used. Root-specific expression of polynucleotides of the invention can be achieved under the control of the root-specific ANR1 promoter (Zhang & Forde, *Science*, 279:407, 1998). Any strong, constitutive promoters, such as the CaMV 35S promoter, can bc used for the expression of polynucleotides of the invention throughout the plant.

Another example of a promoter useful in the present invention is the promoter of the SNF4 gene provided in SEQ ID NO:2 (residues 1-1097). One of skill that the variants of this promoter sequence can also be used. For example, the promoter can be less than full length (e.g. fragments of 500 to about 1000 nucleotides in length) and still provide suitable expression levels. This promoter is usefuil because it responds to diverse stresses (e.g., heat drought, cold) and to abscisic acid. The SNF4 promoters of the invention can also be used to drive expression of heterologous nucleic acid sequences, whose expression would be advantageous under stress conditions. Examples of such nucleic acids include genes that control insect pests or pathogens (bacteria and fungi), such as *Bacillus thuringicesis* toxin, viral coat proteins, chitinases, phytoalexins, and the like. Genes that confer resistance to herbicides include, for example, genes encoding acetohydroxy acid synthase, phosphotransferases. Genes encoding glutathione reductase and superoxide dismutase are useful to confer resistance to fungal toxins and oxidative stress in cold, salinity, drought and wounding.If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *EMBO. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacteriumn tumefaciens* host vector. The virulence functions of the *Agrobacteriun tumcefaciens* host will direct the insertion of the construct and adjacent marker into the plant cell DNA when the cell is infected by the bacteria. *Agrobaciteriuni tumefaciens*-mediated transformation techniques, including disarming and use of binary vectors, are well described in the scientific literature. See, for example Horsch et al. *Science* 233:496–498 (1984), and Fraley et al. *Proc. Natl. Acac. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricincus, Secale, Senecio, Sinapis, Solanum, Sorghum, Theobrmus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of mRNA or protein of the invention in transgenic plants. Means for detecting and quantitating mRNAs or proteins are well known in the art.

Plants with enhanced resistance to stress conditions can be selected in many ways. One of ordinary skill in the art will recognize that the following methods are but a few of the possibilities. One method of selecting plants with enhanced resistance is to determine resistance of a plant to a specific plant stress condition such as heat, cold, or nutritional deprivation. Other possible stress conditions include, but are not limited to, chemicals, metabolic changes (sec, e.g., Agrios, *Plant Pathology* (Academic Press, San Diego, Calif.) (1988)). One of skill in the art will recognize that resistance responses of plants vary depending on many factors, including what particular stress condition or plant is used. Generally, enhanced resistance is measured by the reduction or elimination of stress symptoms when compared to a control plant.

The following Examples are offered by way of illustration, not limitation.

EXAMPLES

Example 1

This example shows the isolation of the LeSNF4 and LeSNF1 cDNAs from tomato genomic library.

A partial cDNA was initially isolated by differential cDNA display con-esponding to a mRNA that was downregulated by gibberellin (GA) in association with tomato seed germination, and subsequently obtained cDNA and gDNA sequence from library screening. Differential Display (DCD) was perfonned according to known techniques.

Southern Blots of tomato genomic DNA suggested that the gene occurs only once in the genome. The gene encodes a 373 amino acid protein with a predicted molecular weight of 41 kD. A comparison of the amino acid sequence to yeast SNF4, mammalian γ-AMPK, and *Phalseolits vulgaris* L. Pv42 predicted protein is shown in FIG. 1. The nucleic acid sequence and the encoded protein sequence of LeSNF4 are shown in SEQ ID NO:1 and SEQ ID NO:3. The genomic sequence is shown in SEQ ID NO:2.

The SNF4 and γ-AMPK proteins contain four repeats of a CBS motif identified from the cystathionine-β-synthase protein. Bateman, A., *Trends Biochem. Sci.* 22:12–13 (1997). This motif appears three times in the predicted tomato amino acid sequence, two near the C-terminal end and a third near the N-tcrminal end. The intervening region where a fourth CBS domain is present in SNF4 and γ-AMPK is not identified as such in LeSNF4; however, this region is very highly conserved between tomato and bean, suggesting a role in protein function. The newly isolated gene is therefore tenned the tomato gene LeSNF4 (*Lycopersicon esculeiltum* SNF4).

Similarly, LeSNF1 gene was isolated from tomato, and the predicted protein has 85% identity and 90% similarity to the tobacco NPK5 protein. The nucleic acid sequence of Le SNF1 is shown in SEQ ID NO:4.

Example 2

This example shows the LeSNF4 gene is a functional homolog of the yeast SNF4 gene.

To test whether LeSNF4 is a functional homolog of the yeast SNF4, cDNA coding for the C-terminal 320 amino acids and the full length 373 amino acids of LeSNF4 (see FIG. 1) were independently transformed into a yeast line containing a deletion in the SNF4 gene (Δ-SNF4) according to standard techniques. The partial cDNA was used since this cDNA encodes a protein that most closely complements the yeast SNF4 protein, in both size and homology. The Δ-SNF4 mutants can grow on glucose, but not on sucrose or other sugars as the sole carbon source, since SNF4 protein is required to activate SNF1 kinase, which in turn derepresses invertase and other genes required to metabolize sucrose and other sugars. Schuller, H. and Entian, K., *Gene* 67:247 (1988); Woods, A., et al., *J. Biol. Chem.* 269:19509 (1994).

As expected, neither the Δ-SNF4 mutant nor the mutant cells transformed with the empty vector grew on medium containing sucrose as the sole carbon source. However, cells transformed with the partial or full length LeSNF4 grew on sucrose-containing medium, demonstrating functional complementation of the SNF4 mutation. Similar results were obtained when galactose was used instead of sucrose as the sole carbon source. Southern hybridization of DNA from the various transformed lines confinmed that the LeSNF4 cDNA was present in the transfonned lines that exhibited growth on sucrose. Therefore, the results of this example show that both the full length 373 or partial 320 amino acids of LeSNF4 are able to functionally substitute for the 322 amino acid yeast SNF4 protein in the glucose repression system, confirming and extending the cross-kingdom parallels in this family of kinases.

Example 3

This example demonstrates that the expression of LeSNF4 and LeSNF1 in plants is affected by environmental and nutritional conditions.

In yeast, transcription of SNF1 and SNF4 is not affected by glucose, and mRNA amounts do not change markedly in response to environmental or nutritional conditions (Celenza and Carlson, *Mol. Cell Biol.* 4:54–60 (1984)). Similarly, some variations of amounts of AMPK mRNAs occur between organs, but differences are not great (Gao, et al., *J. Biol. Chem.* 271:8675–8681 (1996); Mitchelhill, et al., *J. Biol. Chem.* 269:2361–2364). Thus, it has been thought that expression of these genes is essentially constitutive with regulation being primarily biochemical through phosphorylation and dephosphorylation.

With respect to plant SnRKs, a recent review concluded that "little is known about regulation of the plant SNF1-related kinascs in vitro, and almost nothing is known about their regulation in vivo ". (Hardie, D., el al., *Annu. Rev. Biochem.* 67:821–55 (1998)). Since LeSNF4 was originally identified based on its differential expression during germination and exposure to GA, suggesting honnonal and/or developmental regulation of transcription, the mRNA expression patterns of LeSNF1 and LeSNF4 were further investigated.

LeSNF4 and LeSNF1 transcripts were examined in wild type tomato (cv. Moneymaker) seeds under a range of conditions that influence germination. LeSNF4 mRNA is abundant in dry seeds and those seeds that have not completed germination after 48 hours; but disappears completely in germinated seeds. LeSNF1 transcripts were also abundant in dry seeds and seeds that had not genninated after 48 hours imbibition, but persisted in germinated seeds. Imbibing seeds in ABA, 1.2 MPa PEG osmotic solution, or under far-red irradiation, all of which inhibit radicle emergence, maintain the LeSNF4 mRNA at high levels.

In contrast, LeSNF1 transcript levels were not maintained by exogenous ABA or osmoticum and only partly by far-red illumination. LeSNF4 mRNA was abundant in naturally dormant seeds that had not germinated after 14 days imbibition on water and in those seeds that failed to germinated when transferred to GA, but disappeared with 48 hours in those seeds that germinated when transferred to GA; LeSNF1 was also present in dormant seeds but persisted on subsequent treatment with GA, irrespective of germination capacity. In each case, LeSNF4 mRNA is present under conditions where radicle emergence does not occur and disappears in seeds that complete germination; whereas LeSNF1 transcripts were largely unaffected by different treatments.

The SNF1/AMPK complex has been suggested to be a stress response system (Hardie, supra.) In addition, many genes expressed during late embryogenesis are also expressed in vegetative tissues during periods of physiological water stress or in response to ABA. Therefore, the expression of LeSNF4 and LeSNF1 was examined in seedling leaves subjected to various forms of water stress. A single foliar spray of ABA induced LeSNF4 expression within 6 hours; subsequently mRNA levels decreased and had disappeared by 24 hours. LeSNF4 was abundantly and rapidly expressed by excision and dehydration, transiently during cold treatment, and to a lesser extent during the heat stress. In contrast, none of the imposed conditions significantly affected abundance of LeSNF1 mRNA.

It is interesting to note that the LeSNF4 expression is rapidly and dramatically up-regulated in response to physiological water stress and exogenous ABA, while the LeSNF1 is largely constitutively expressed and unaffected by exogenous hormones. Similarly there is little evidence for transcriptional regulation of the SNF1 homologs in potato and tobacco, and it has been suggested that SnRKs may have a function in basic physiological processes in plant cells. Krapp, et al., *Plant J.* 3:817–828 (1993); Mumaka, et al., supra.).

Based on the results presented here SNF 1-related protein kinases are involved in multiple signal transduction and/or regulation pathways, while only some of these functions may require and/or be regulated by SNF4-like proteins. For example, the tobacco and barley SNF1-related kinases are able to phosphorylate HMG-CoA reductase without SNF4 protein, at least in vitro . Barker, et al., *Plant Physiol.* 112:1141–1149 (1996); Muranaka, et al., *Plant Cell Physiol.* (Suppl) 38:02 (1997). On the other hand, SNF4 proteins may be required to react to any stress that alters cellular energy status or sugar supply or requires alteration in sugar partitioning.

By analogy with the yeast system, plant SNF1-related protein kinases play a role in sugar sensing. Jang and Sheen, supra.; Smeekens and Rook, *Plant Physiol.* 115:7–13 (1997)). Sugars control the expression of many plant genes, and thereby influence photosynthesis, metabolic processes and developmental transitions throughout the plant life cycle. At least three pathways have been identified for sugar sensing in plants, and SnRKs have been implicated as downstream factors in signal transduction. rotein phosphorylation/dephosphorylation is involved in diverse signaling pathways throughout plant development, including those in developing and germinating seeds (Halford and Hardie *Plant Mol. Biol.* 37:735–748 (1998); Geogatsos, and Fisentzides, *Protein Phosphorylationi in Plants* (Clarendon) 141:152; Walker-Simmons, *Seed Sci. Res.* 8:193–200 (1998)) and an intriguing hypothesis has been put forward invoking this reversible process as a time-keeping mechanism in seed dormancy (Trewavas, A., *BioEssays*, 6:87–92 (1998)).

Glucose is generally absent or present at low levels in mature seeds, while sucrose accumulates to high concentrations. Amuti, K. and Pollard, C., *Phytochem.* 16:529–532 (1977). There is strong evidence that soluble sugars, particularly sucrose and oligosaccharides such as raffinose and stachyose, are involved in desiccation tolerance and longevity in seeds, and in vegetative water and cold stress. Therefore, under these conditions carbohydrate metabolism is directed to conserve and/or accumulate these sugars, rather than use them as an immediate energy source. Recently direct evidence for the role of sugars in seed development has begun to emerge. During seed development, the change from cell division to cell differentiation is accompanied by a reduction in hexose concentration and increase in sucrose levels (Borisjuk, et al., *Plant J.* 15:583–591 (1998)). In order to investigate the role of sugar status and carbon partitioning in developing seeds, Weber, et al., *Plant J.* 16:163–172 (1998), expressed a yeast invertase gene in maturing embryos of Vicia narbonensis. The transgenic cotyledons showed a marked reduction in sucrose and elevated hexose levels causing a fall in starch and storage protein accumulation. In addition genes of sucrose and starch metabolism were specifically down regulated. These results suggest that a sucrose specific sensing mechanism in the storage cells senses sucrose and initiates storage associated differentiation.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. An isolated nucleic acid molecule comprising a polynucleotide sequence encoding a functional plant SNF4 polypeptide, wherein the polypeptide comprises an amino acid sequence that has at least about 70% identity to SEQ ID NO:3.

2. The nucleic acid molecule of claim 1, wherein the polynucleotide sequence specifically hybridizes to SEQ ID NO: 1 or its complement, or SEQ ID NO:2 or its complement.

3. The nucleic acid molecule of claim 1, wherein the SNF4 polypeptide is as shown in SEQ ID NO: 3.

4. The nucleic acid molecule of claim 1, wherein the polynucleotide sequence is as shown in SEQ ID NO: 1.

5. A recombinant expression vector comprising the polynucleotide sequence of claim 1.

6. The recombinant expression vector of claim 5, further comprising a promoter operably linked to the polynucleotide sequence.

7. The recombinant expression vector of claim 6, wherein the promoter is a constitutive promoter.

8. The recombinant expression vector of claim 6, wherein the promoter is an inducible promoter.

9. A host cell transformed with the recombinant expression vector of claim 5.

10. A transgenic plant comprising a recombinant expression cassette comprising a promoter operably linked to a polynucleotide sequence of claim 1.

11. The transgenic plant of claim 10, wherein the plant is tomato.

12. The transgenic plant of claim 10, wherein the polynucleotide sequence specifically hybridizes to SEQ ID NO: 1 or its complement, or SEQ ID NO: 2 or its complement.

13. The transgenic plant of claim 10, wherein the polypeptide is as shown in SEQ ID NO:3.

14. A method of modulating sugar metabolism in a plant, the method comprising a) introducing into the plant a recombinant expression vector comprising a promoter operably linked to a polynucleotide sequence encoding a functional plant SNF4 polypeptide, wherein the polypeptide comprises an amino acid sequence that has at least about 70% identity to SEQ ID NO: 3; and b) selecting a plant with modulated sugar metabolism.

15. The method of claim 14, wherein the polynucleotide specifically hybridizes to SEQ ID NO: 1 or its complement, or SEQ ID NO: 2 or its complement.

16. The method of claim 14, wherein the polypeptide is as shown in SEQ ID NO: 3.

17. The method of claim 14, wherein the modulation of sugar metabolism is associated with a response to stress conditions.

* * * * *

SEQUENCE LISTING

<160> NUMBER OF SEQ ID NOS: 7

<210> SEQ ID NO 1
<211> LENGTH: 1262
<212> TYPE: DNA
<213> ORGANISM: Lycopersicon esculentum
<220> FEATURE:
<223> OTHER INFORMATION: Lycopersicon esculentum plant homolog of yeast
      sucrose nonfermenting 4 (SNF4) activation subunit of protein
      kinase (LeSNF4)

<400> SEQUENCE: 1

```
ctctttgttt cacccagcac acaaaatttt aaaaaaaaaa tactcataca aacaaaatgc      60
aggcaacagc ggagatacaa gcggcgggaa gccctcgtag atctcagaag catcagatgc     120
ttaaagacaa gcaggtgaag gatctaatta ttgataaaag gagacttgtg gaggttccgt     180
atacagccac gctggcagat acaataaaca ctctgatggc taacaaggtg gtggcggttc     240
cggtggctgc accgcctggg cactggattg gcgccggcgg ttctatgatt ttggaatctg     300
ataaacagac gggtgctgta cgaaaacatt atatagggat ggtaactatg cttgatattc     360
tcgcatatat tgctggaaac ggttatcgtg atgatgatga tgatcttacg aaaaagatga     420
tggttcctgt ttcttcgatt attgggcatt gtcttgaaag tcttagtttg tggaccctca     480
gccctaacac aagtattgtg gattgtatgg aagttttcag caaaggcata catcgagcca     540
tggtaccagt gaatggacga ttagaaaatg tagttggcgt tgagctcacc gagtcagcgt     600
catgttaccg aatgctaaca caaatggatc tgcttaggtt tttgaatgac cagcaggagc     660
ttaaagcgat catgtcgcac aaggtctcgg ataaacaact ccaagcaatc acagacactg     720
ttttcggtgt gactaataag gcgaaagtta tcgatgtgat caaatgcatg agaacagctt     780
cactaaatgc agtaccaatt gtggagtcat ccaatgacat aacagaagat catactcagc     840
ttgtgaatgg gaaaaagagg aagattgtag gaacattttc agcaacggac ttgagaggct     900
gtcctgtatc gaaaatgcag cctctattga acctagaggt cctcgatttc ttgaaaatgc     960
tgtcgggagc tcctaatacc gggctgagat cttcatggag ggaacaagtg acatgccgcc    1020
ccgaatcgtc actcggggaa gtggtagaga aagttgtttc agacaatgtg catcgtgttt    1080
gggtggtgga tgaacaaggc ttgctggaag gagttgtatc cctaactgac atgataagag    1140
tcatcagact ctggtatctt actgagtttt tgcagtgatg tgtagttgtt gtacacactc    1200
ttttgcaccc gttttgttct ggttggtgtt ttggtgtata aatgaaatgc aatctgttta    1260
tc                                                                   1262
```

<210> SEQ ID NO 2
<211> LENGTH: 3019
<212> TYPE: DNA
<213> ORGANISM: Lycopersicon esculentum
<220> FEATURE:
<221> NAME/KEY: modified_base
<222> LOCATION: (737)
<223> OTHER INFORMATION: n = any nucleotide
<220> FEATURE:
<221> NAME/KEY: promoter
<222> LOCATION: (1)..(1097)
<220> FEATURE:
<221> NAME/KEY: CDS
<222> LOCATION: join(1235..1669, 1995..2351, 2446..2775)
<223> OTHER INFORMATION: Lycopersicon esculentum sucrose non-fermenting protein kinase activation subunit 4 (LeSNF4)

<400> SEQUENCE: 2

```
aagcggtcac attttttaag aagatggtta tctcaatcaa catcttggat accaaaaaag    60
aaagccttag cctaacctag acaatccctt cactttgcta ccgggtgcgt ctgtctaact   120
ttgaattaac tagggctgag aaactggtca gttaaagtta aatggtgtct tatatactgt   180
tgaatatgag gatctttaga tatattcttt atttgtttat tgaataggtt gtcaatccga   240
agttgttact gctaattcaa ttattattat ggctttggat gcttacccaa ttactcataa   300
tctcttcttc ttgcagatga tagcagctaa tttcttgttc atagagaaat atacatcata   360
attccatacg ccctctttct gtttctttta ccttctaatc cactagacaa agtgctaggg   420
tggacctaaa cgaggctccc tccgtcctat tttacgtgat acttttttaaa ttttaaataa   480 attaattttt tatcataaat tttttataaa tattttaaca ttttaaatta taatatattt   540
tgatttatta taatatttac gtaatttata aatatataaa atttatttat aaattttttaa   600 ttaaatttaa attatttaac tctaattgaa aaatacttaa ctaacgataa atggaaagag   660
aaggagtatt tgataattgc catttcatga ttcatgatgg aagtttcaga tacaaattaa   720
ttggaataag aataacngt attcattata aaaaagact ctaaaactg ttttggtacg   780 tggatggata gaccaaaata tccgtgatat tatttttattt aagtttttat atgtgacggt   840
aaagataaag ttagattttg agcaagaaat ttaaaatata aaaaaatact tacagacaaa   900
aagttggaac gaatgtgtag agccttgcta acacctccgg ctctaacagg agttttacta   960
tcatgataca ataatactt cgaattaaat taaatatgag ataaatttcc acgtaccaaa  1020
tgacccaact ggataggatc ggtgtattgc tcaagaagca agcaccacgt agcaaacaaa  1080
ataacaaatg gcactcttct cttttttcatc ccctaatgct gacacgtatt aagccacata  1140
tgaacctata ttagtgcact ttcagttttt caacttcctc tttgttttca cccagcacac  1200
aaaatttttt taaaaaaata ctcatacaaa caaa atg cag gca aca gcg gag         1252
                                      Met Gln Ala Thr Ala Glu
                                        1               5 ata caa gcg gcg gga agc cct cgt aga tcc cag aag cat cag atg ctt     1300
Ile Gln Ala Ala Gly Ser Pro Arg Arg Ser Gln Lys His Gln Met Leu
         10                  15                  20 aaa gac aag cag gtg aag gat cta att att gat aaa agg aga ctt gtg     1348
Lys Asp Lys Gln Val Lys Asp Leu Ile Ile Asp Lys Arg Arg Leu Val
     25                  30                  35 gag gtt ccg tat aca gcc acg ctg gca gat aca ata aac act ctg atg     1396
Glu Val Pro Tyr Thr Ala Thr Leu Ala Asp Thr Ile Asn Thr Leu Met
 40                  45                  50 gct aac aag gtg gtg gcg gtt ccg gtg gct gca ccg cct ggg cac tgg     1444
Ala Asn Lys Val Val Ala Val Pro Val Ala Ala Pro Pro Gly His Trp
```

```
             55                  60                  65                  70
att ggc gcc ggc ggt tct atg att ttg gaa tct gat aaa cag acg ggt          1492
Ile Gly Ala Gly Gly Ser Met Ile Leu Glu Ser Asp Lys Gln Thr Gly
                75                  80                  85 gct gta cga aaa cat tat ata ggg atg gta act atg ctt gat att ctc          1540
Ala Val Arg Lys His Tyr Ile Gly Met Val Thr Met Leu Asp Ile Leu
            90                  95                 100 gca tat att gct gga aac ggt tat cgt gat gat gat gat ctt acg              1588
Ala Tyr Ile Ala Gly Asn Gly Tyr Arg Asp Asp Asp Asp Leu Thr
        105                 110                 115 aaa aag atg atg gtt cct gtt tct tcg att att ggg cat tgt ctt gaa          1636
Lys Lys Met Met Val Pro Val Ser Ser Ile Ile Gly His Cys Leu Glu
    120                 125                 130 agt ctt agt ttg tgg acc ctc agc cct aac aca aggtatgtaa cgaggaattg        1689
Ser Leu Ser Leu Trp Thr Leu Ser Pro Asn Thr
135                 140                 145 agatctcttg gccgcttaca aaataaaaa ctgatgttct cctcatgggt aaaaatgaag         1749
aggagatcac agaactaaga aaattaagaa attattatga gtaacctaca aaatgaatcc        1809
tgtagaaagt agtggatgtt gttagcaaat acttttaatc tatcaaattg gaatcggagt        1869
aaggattttt ataattatga ttacttcaat aaagtccttg ctgctatttg tcaaatgaat        1929
tttggatatt caaggtatta tctaattttg caaatgtatc ttacgaattg attctttata        1989 tgtga agt att gtg gat tgt atg gaa gtt ttc agc aaa ggc ata cat            2036
      Ser Ile Val Asp Cys Met Glu Val Phe Ser Lys Gly Ile His
                      150                 155 cga gcc atg gta cca gtg aat gga cga tta gaa aat gta gtt ggc gtt          2084
Arg Ala Met Val Pro Val Asn Gly Arg Leu Glu Asn Val Val Gly Val
160                 165                 170                 175 gag ctc acc gag tca gcg tca tgt tac cga atg cta aca caa atg gat          2132
Glu Leu Thr Glu Ser Ala Ser Cys Tyr Arg Met Leu Thr Gln Met Asp
                180                 185                 190 ctg ctt agg ttt ttg aat gac cag cag gag ctt aaa gcg atc atg tcg          2180
Leu Leu Arg Phe Leu Asn Asp Gln Gln Glu Leu Lys Ala Ile Met Ser
            195                 200                 205 cac aag gtc tcg gat aaa caa ctc caa gca atc aca gac act gtt ttc          2228
His Lys Val Ser Asp Lys Gln Leu Gln Ala Ile Thr Asp Thr Val Phe
        210                 215                 220 ggt gtg act aat aag gcg aaa gtt atc gat gtg atc aaa tgc atg aga          2276
Gly Val Thr Asn Lys Ala Lys Val Ile Asp Val Ile Lys Cys Met Arg
    225                 230                 235 aca gct tca cta aat gca gta cca att gtg gag tca tcc aat gac ata          2324
Thr Ala Ser Leu Asn Ala Val Pro Ile Val Glu Ser Ser Asn Asp Ile
240                 245                 250                 255 aca gaa gat cat act cag ctt gtg aat gtaagttaaa acatttagtc                2371
Thr Glu Asp His Thr Gln Leu Val Asn
                260 tcactcgttt gaatttaatt tatatatata cctcttaacg atatcaggat tattgttttc        2431 tatgaaatat acag ggg aaa aag agg aag att gta gga aca ttt tca gca         2481
                Gly Lys Lys Arg Lys Ile Val Gly Thr Phe Ser Ala
                            265                 270                 275 acg gac ttg aga ggc tgt cct gta tcg aaa atg cag cct cta ttg aac          2529
Thr Asp Leu Arg Gly Cys Pro Val Ser Lys Met Gln Pro Leu Leu Asn
        280                 285                 290 cta gag gtc ctc gat ttc ttg aaa atg ctg tcg gga gct cct aat acc          2577
Leu Glu Val Leu Asp Phe Leu Lys Met Leu Ser Gly Ala Pro Asn Thr
    295                 300                 305 ggg ctg aga tct tca tgg agg gaa caa gtg aca tgc cgc ccc gaa tcg          2625
```

```
Gly Leu Arg Ser Ser Trp Arg Glu Gln Val Thr Cys Arg Pro Glu Ser
    310                 315                 320 tca ctc ggg gaa gtg gta gag aaa gtt gtt tca gac aat gtg cat cgt     2673
Ser Leu Gly Glu Val Val Glu Lys Val Val Ser Asp Asn Val His Arg
325                 330                 335                 340 gtt tgg gtg gtg gat gaa caa ggc ttg ctg gaa gga gtt gta tcc cta     2721
Val Trp Val Val Asp Glu Gln Gly Leu Leu Glu Gly Val Val Ser Leu
                345                 350                 355 act gac atg ata aga gtc atc aga ctc tgg tat ctt act gag ttt ttg     2769
Thr Asp Met Ile Arg Val Ile Arg Leu Trp Tyr Leu Thr Glu Phe Leu
            360                 365                 370 cag tgatgtgtag ttgttgtacg cactcttttg cacccgtttt gttctggttg          2822
Gln gtgttttggt gtataaatga aatgcaatct gtttatcaaa tgatcagttc tcattctgaa   2882
aatttgtttt gtgtcttaca caagcgaccc taaaggaaaa caataggtac tactagattg   2942 aaattttct accatatcgc tttcatataa ttattaatga acactactct tatgttccgg    3002
ggacaaacat aaagctt                                                  3019

<210> SEQ ID NO 3
<211> LENGTH: 373
<212> TYPE: PRT
<213> ORGANISM: Lycopersicon esculentum
<220> FEATURE:
<223> OTHER INFORMATION: Lycopersicon esculentum sucrose non-fermenting
      protein kinase activation subunit 4 (LeSNF4)

<400> SEQUENCE: 3

Met Gln Ala Thr Ala Glu Ile Gln Ala Ala Gly Ser Pro Arg Arg Ser
1               5                   10                  15

Gln Lys His Gln Met Leu Lys Asp Lys Gln Val Lys Asp Leu Ile Ile
            20                  25                  30

Asp Lys Arg Arg Leu Val Glu Val Pro Tyr Thr Ala Thr Leu Ala Asp
        35                  40                  45

Thr Ile Asn Thr Leu Met Ala Asn Lys Val Val Ala Val Pro Val Ala
    50                  55                  60

Ala Pro Pro Gly His Trp Ile Gly Ala Gly Gly Ser Met Ile Leu Glu
65                  70                  75                  80

Ser Asp Lys Gln Thr Gly Ala Val Arg Lys His Tyr Ile Gly Met Val
                85                  90                  95

Thr Met Leu Asp Ile Leu Ala Tyr Ile Ala Gly Asn Gly Tyr Arg Asp
            100                 105                 110

Asp Asp Asp Asp Leu Thr Lys Lys Met Met Val Pro Val Ser Ser Ile
        115                 120                 125

Ile Gly His Cys Leu Glu Ser Leu Ser Leu Trp Thr Leu Ser Pro Asn
    130                 135                 140

Thr Ser Ile Val Asp Cys Met Glu Val Phe Ser Lys Gly Ile His Arg
145                 150                 155                 160

Ala Met Val Pro Val Asn Gly Arg Leu Glu Asn Val Gly Val Glu
                165                 170                 175

Leu Thr Glu Ser Ala Ser Cys Tyr Arg Met Leu Thr Gln Met Asp Leu
            180                 185                 190

Leu Arg Phe Leu Asn Asp Gln Gln Glu Leu Lys Ala Ile Met Ser His
        195                 200                 205

Lys Val Ser Asp Lys Gln Leu Gln Ala Ile Thr Asp Thr Val Phe Gly
    210                 215                 220
```

-continued

| Val | Thr | Asn | Lys | Ala | Lys | Val | Ile | Asp | Val | Ile | Lys | Cys | Met | Arg | Thr |
| 225 | | | | 230 | | | | | 235 | | | | | 240 | |

| Ala | Ser | Leu | Asn | Ala | Val | Pro | Ile | Val | Glu | Ser | Ser | Asn | Asp | Ile | Thr |
| | | | | 245 | | | | | 250 | | | | | 255 | |

| Glu | Asp | His | Thr | Gln | Leu | Val | Asn | Gly | Lys | Lys | Arg | Lys | Ile | Val | Gly |
| | | | 260 | | | | | 265 | | | | | 270 | | |

| Thr | Phe | Ser | Ala | Thr | Asp | Leu | Arg | Gly | Cys | Pro | Val | Ser | Lys | Met | Gln |
| | | 275 | | | | | 280 | | | | | 285 | | | |

| Pro | Leu | Leu | Asn | Leu | Glu | Val | Leu | Asp | Phe | Leu | Lys | Met | Leu | Ser | Gly |
| | 290 | | | | | 295 | | | | | 300 | | | | |

| Ala | Pro | Asn | Thr | Gly | Leu | Arg | Ser | Ser | Trp | Arg | Glu | Gln | Val | Thr | Cys |
| 305 | | | | 310 | | | | | 315 | | | | | 320 | |

| Arg | Pro | Glu | Ser | Ser | Leu | Gly | Glu | Val | Val | Glu | Lys | Val | Val | Ser | Asp |
| | | | | 325 | | | | | 330 | | | | | 335 | |

| Asn | Val | His | Arg | Val | Trp | Val | Val | Asp | Glu | Gln | Gly | Leu | Leu | Glu | Gly |
| | | | 340 | | | | | 345 | | | | | 350 | | |

| Val | Val | Ser | Leu | Thr | Asp | Met | Ile | Arg | Val | Ile | Arg | Leu | Trp | Tyr | Leu |
| | | 355 | | | | | 360 | | | | | 365 | | | |

| Thr | Glu | Phe | Leu | Gln |
| | 370 | | | |

<210> SEQ ID NO 4
<211> LENGTH: 1929
<212> TYPE: DNA
<213> ORGANISM: Lycopersicon esculentum
<220> FEATURE:
<223> OTHER INFORMATION: Lycopersicon esculentum plant homolog of yeast
      SNF1 kinase subunit of protein kinase (LeSNF1)

<400> SEQUENCE: 4

```
ggcacgaggt ggaaggaaaa catcaaagga aaatggacgg aacagcagtg cagggcacca      60
gcagtgttga ctcattttta cggaactata aactcgggaa acacttggc  attggatcgt     120
tcggcaaagt taaaatagct gaacatacgt taacagggca caaagttgct gtcaagattc     180
ttaatcgtcg aaaaatcagg aatatggaca tggaggagaa agtccgtaga gaaatcaaaa     240
tattgagatt gttcatgcat cctcatatta tacggcttta tgaggtcata gagacaccat     300
cagatatata tgttgtgatg gagtatgtga atctggcga gttatttgat tacattgttg     360
agaagggcag attgcaggag gatgaagctc gtaacttttt tcagcagata atttctggtg     420
tggagtactg ccatagaaac atggtggttc atagagacct taagcctgaa aacctccttc     480
tggactccaa atggaatgtg aagatcgcag attttggttt gagcaatatc atgcgcgatg     540
gtcattttct gaagacaagt tgcggaagcc caaactatgc tgcccagag gttatatcag     600
gtaaattgta tgctggccct gaggtagatg tatggagctg tggtgttatt ctttatgctc     660
ttctctgtgg caccctccg tttgacgatg aaacatacc caatctttt aagaaaataa     720
agggtggaat atatactctg cccagccatt tatcagctgg tgcgagggat ttgattccga     780
ggatgcttat agtcgaccca atgaagcgaa tgactattcc tgagattcgc ctgcacccctt     840
ggttccaagc tcatttgcca cgctatttgg ccgtgcctcc accagataca acccaacaag     900
caaagaagat cgatgaagag attcttcaag aggtggttaa gatgggattt gacaggaaca     960
accttactga gtctcttcgc aatagagttc aaaatgaggg cactgttgca tactatctgc    1020
tcctggacaa tcgccatcgt gtttccactg gctatcttgg agctgaattt caggagtcca    1080
tggaatatgg ttacaaccgg atcaattcta atgaaaccgc tgcttcccct gttggtcaac    1140
```

-continued

```
gtttcccagg aataatggat tatcagcaag ctggtgcaag acagttcccc attgaaagaa    1200
aatgggctct tggcctccag tctcgagcgc atccacgtga ataatgact gaagttttga     1260 aagctctgca agaactgaat gtatgttgga aagattggt cagtataaca tgaaatgtcg     1320
atgggttcct agcttacctg gtcatcatga aggcatgggt gttaattcca tgcatgggaa    1380
tcagttcttt ggagatgatt catccatcat tgagaatgat ggggccacaa agttaacaaa    1440
tgtggtcaag tttgaagttc agctttacaa aaccagggag gagaagtact tgcttgacct    1500
tcagagactt cagggtccac aattcctctt cctggatctc tgtgctgctt ttcttgctca    1560
gcttcgagta ctttaaagtc tccgaaataa ggagctaagt tggaaaaagc ccatgcttgt    1620 ataattgg taccagct cagttactgc attttgtctt gttaacaaat tccaccctgc        1680
ttggtcagag gtgcctagca actctttttt tcttttgatt cgctaggaga tctagctcac    1740
tctctttttt aacgtttatg gaatttcagt tacctacagt atctacttac agattgaact    1800
gcaagatgag cgcgatgtct gtctgtgacc cattccctct tctccccta tcgacgatca     1860 tttggagtcc aacgaagatt ttcttgtgtc aaatttgaaa tgtttgtctg aataaaaaca    1920
agtcccaac                                                            1929
```

<210> SEQ ID NO 5
<211> LENGTH: 379
<212> TYPE: PRT
<213> ORGANISM: Phaseolus vulgaris
<220> FEATURE:
<223> OTHER INFORMATION: Phaseolus vulgaris L. Pv42

<400> SEQUENCE: 5

```
Met Gln Glu Val Lys Gly Ala Thr Met Gln Arg Ser Arg Ser Val Arg
  1               5                  10                  15

Leu Lys Glu Lys Lys Val Lys Asp Met Met Val Gly Lys Lys Arg Leu
             20                  25                  30

Val Glu Val Pro Tyr Thr Ala Ser Leu Ala Gln Ile Met Asn Thr Leu
         35                  40                  45

Val Ala Asn Lys Ile Val Ala Val Pro Val Ala Ala Pro Pro Gly Gln
     50                  55                  60

Trp Ile Gly Ala Gly Gly Ser Met Ile Val Glu Ser Asp Lys Gln Thr
 65                  70                  75                  80

Gly Ala Val Arg Lys His Tyr Ile Gly Met Val Thr Met Leu Asp Ile
                 85                  90                  95

Leu Ala His Ile Ala Gly Asp Asp His Leu Ser Cys Gly Asp Asn Ile
            100                 105                 110

Thr Gln Asp Leu Asp Gln Arg Met Ser Asp Ser Val Ser Ser Ile Ile
        115                 120                 125

Gly His Ser Phe Glu Gly Leu Ser Leu Trp Thr Leu Asn Pro Asn Thr
    130                 135                 140

Ser Met Leu Asp Cys Met Glu Val Phe Ser Lys Gly Val His Arg Ala
145                 150                 155                 160

Met Val Pro Val Asp Gly Leu Glu Glu Asn Val Ala Ser Gly Val Glu
                165                 170                 175

Leu Thr Glu Ser Ala Ser Ser Tyr Gln Met Leu Thr Gln Met Asp Met
            180                 185                 190

Leu Lys Phe Leu His Gly Gly Ala Glu Leu His Ser Ile Leu Ser
        195                 200                 205

Arg Ser Val Gln Asp Leu Gly Ala Asp Thr Val Gln Ile Tyr Ala Ile
    210                 215                 220
```

-continued

```
Thr Asp Arg Thr Lys Leu Val His Ala Ile Lys Cys Leu Lys Ala Ala
225                 230                 235                 240

Met Leu Asn Ala Val Pro Ile Val Arg Ala Thr Gly Val Gly Gln Asp
            245                 250                 255

Asp His Lys Gln Leu Ile Asn Gly Arg Cys Arg Lys Leu Ile Gly Thr
            260                 265                 270

Phe Ser Ala Thr Asp Leu Arg Gly Cys His Ile Ser Ser Leu Lys Ser
            275                 280                 285

Trp Leu Gly Ile Ser Ala Leu Ala Phe Thr Glu Glu Val Arg Ser Ser
        290                 295                 300

Pro Leu Tyr Ser Glu Ser Asp Met Gln Asn Arg Gly Ser Ser Arg Arg
305                 310                 315                 320

Glu Leu Val Thr Cys Tyr Ala Glu Ser Pro Leu Ser Glu Val Ile Glu
                325                 330                 335

Lys Ala Val Thr Ser His Val His Arg Val Trp Val Val Asp Gln Glu
            340                 345                 350

Gly Leu Leu Val Gly Val Val Ser Leu Thr Asp Val Ile Arg Val Ile
            355                 360                 365

Arg His Ser Leu Leu Ser Asp Ser Asn Asp Gln
        370                 375

<210> SEQ ID NO 6
<211> LENGTH: 330
<212> TYPE: PRT
<213> ORGANISM: Rattus norvegicus
<220> FEATURE:
<223> OTHER INFORMATION: gamma subunit of AMP-activated protein kinase
      (AMPK-gamma)

<400> SEQUENCE: 6

Met Glu Ser Val Ala Ala Glu Ser Ala Pro Ala Pro Glu Asn Glu His
1               5                   10                  15

Ser Gln Glu Thr Pro Glu Ser Asn Ser Ser Val Tyr Thr Thr Phe Met
            20                  25                  30

Lys Ser His Arg Cys Tyr Asp Leu Ile Pro Thr Ser Ser Lys Leu Val
        35                  40                  45

Val Phe Asp Thr Ser Leu Gln Val Lys Lys Ala Phe Phe Ala Leu Val
    50                  55                  60

Thr Asn Gly Val Arg Ala Ala Pro Leu Trp Asp Ser Lys Lys Gln Ser
65                  70                  75                  80

Phe Val Gly Met Leu Thr Ile Thr Asp Phe Ile Asn Ile Leu His Arg
                85                  90                  95

Tyr Tyr Lys Ser Ala Leu Val Gln Ile Tyr Glu Leu Glu Glu His Lys
            100                 105                 110

Ile Glu Thr Trp Arg Glu Val Tyr Leu Gln Asp Ser Phe Lys Pro Leu
        115                 120                 125

Val Cys Ile Ser Pro Asn Ala Ser Leu Phe Asp Ala Val Ser Ser Leu
    130                 135                 140

Ile Arg Asn Lys Ile His Arg Leu Pro Val Ile Asp Pro Glu Ser Gly
145                 150                 155                 160

Asn Thr Leu Tyr Ile Leu Thr His Lys Arg Ile Leu Lys Phe Leu Lys
                165                 170                 175

Leu Phe Ile Thr Glu Phe Pro Lys Pro Glu Phe Met Ser Lys Ser Leu
            180                 185                 190

Glu Glu Leu Gln Ile Gly Thr Tyr Ala Asn Ile Ala Met Val Arg Thr
```

```
            195                 200                 205
Thr Thr Pro Val Tyr Val Ala Leu Gly Ile Phe Val Gln His Arg Val
    210                 215                 220

Ser Ala Leu Pro Val Val Asp Glu Lys Gly Arg Val Val Asp Ile Tyr
225                 230                 235                 240

Ser Lys Phe Asp Val Ile Asn Leu Ala Ala Glu Lys Thr Tyr Asn Asn
                245                 250                 255

Leu Asp Val Ser Val Thr Lys Ala Leu Gln His Arg Ser His Tyr Phe
                260                 265                 270

Glu Gly Val Leu Lys Cys Tyr Leu His Glu Thr Leu Glu Ala Ile Ile
                275                 280                 285

Asn Arg Leu Val Glu Ala Glu Val His Arg Leu Val Val Asp Glu
    290                 295                 300

His Asp Val Val Lys Gly Ile Val Ser Leu Ser Asp Ile Leu Gln Ala
305                 310                 315                 320

Leu Val Leu Thr Gly Gly Glu Lys Lys Pro
                325                 330

<210> SEQ ID NO 7
<211> LENGTH: 322
<212> TYPE: PRT
<213> ORGANISM: Saccharomyces cerevisiae
<220> FEATURE:
<223> OTHER INFORMATION: yeast sucrose nonfermenting protein kinase 1
      kinase subunit (SNF1)

<400> SEQUENCE: 7

Met Lys Pro Thr Gln Asp Ser Gln Glu Lys Val Ser Ile Glu Gln Gln
1               5                   10                  15

Leu Ala Val Glu Ser Ile Arg Lys Phe Leu Asn Ser Lys Thr Ser Tyr
                20                  25                  30

Asp Val Leu Pro Val Ser Tyr Arg Leu Ile Val Leu Asp Thr Ser Leu
            35                  40                  45

Leu Val Lys Lys Ser Leu Asn Val Leu Leu Gln Asn Ser Ile Val Ser
        50                  55                  60

Ala Pro Leu Trp Asp Ser Lys Thr Ser Arg Phe Ala Gly Leu Leu Thr
65                  70                  75                  80

Thr Thr Asp Phe Ile Asn Val Ile Gln Tyr Tyr Phe Ser Asn Pro Asp
                85                  90                  95

Lys Phe Glu Leu Val Asp Lys Leu Gln Leu Asp Gly Leu Lys Asp Ile
                100                 105                 110

Glu Arg Ala Leu Gly Val Asp Gln Leu Asp Thr Ala Ser Ile His Pro
            115                 120                 125

Ser Arg Pro Leu Phe Glu Ala Cys Leu Lys Met Leu Glu Ser Arg Ser
        130                 135                 140

Gly Arg Ile Pro Leu Ile Asp Gln Asp Glu Glu Thr His Arg Glu Ile
145                 150                 155                 160

Val Val Ser Val Leu Thr Gln Tyr Arg Ile Leu Lys Phe Val Ala Leu
                165                 170                 175

Asn Cys Arg Glu Thr His Phe Leu Lys Ile Pro Ile Gly Asp Leu Asn
                180                 185                 190

Ile Ile Thr Gln Asp Asn Met Lys Ser Cys Gln Met Thr Thr Pro Val
            195                 200                 205

Ile Asp Val Ile Gln Met Leu Thr Gln Gly Arg Val Ser Ser Val Pro
        210                 215                 220
```

```
                                    -continued

Ile Ile Asp Glu Asn Gly Tyr Leu Ile Asn Val Tyr Glu Ala Tyr Asp
225                 230                 235                 240

Val Leu Gly Leu Ile Lys Gly Gly Ile Tyr Asn Asp Leu Ser Leu Ser
                245                 250                 255

Val Gly Glu Ala Leu Met Arg Arg Ser Asp Asp Phe Glu Gly Val Tyr
                260                 265                 270

Thr Cys Thr Lys Asn Asp Lys Leu Ser Thr Ile Met Asp Asn Ile Arg
        275                 280                 285

Lys Ala Arg Val His Arg Phe Phe Val Val Asp Asp Val Gly Arg Leu
        290                 295                 300

Val Gly Val Leu Thr Leu Ser Asp Ile Leu Lys Tyr Ile Leu Leu Gly
305                 310                 315                 320

Ser Asn
```